United States Patent
Lyday

(10) Patent No.: US 10,946,080 B2
(45) Date of Patent: *Mar. 16, 2021

(54) COMPOSITIONS AND METHODS FOR COMBINATION THERAPY WITH DENGUE VIRUS AND DENDRITIC CELLS

(71) Applicant: PrimeVax Immuno-Oncology, Inc., Orange, CA (US)

(72) Inventor: Bruce W. Lyday, Orange, CA (US)

(73) Assignee: PRIMEVAX IMMUNO-ONCOLOGY, INC., Orange, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/389,445

(22) Filed: Apr. 19, 2019

(65) Prior Publication Data

US 2019/0247479 A1    Aug. 15, 2019

Related U.S. Application Data

(63) Continuation of application No. 16/172,487, filed on Oct. 26, 2018, now Pat. No. 10,357,553, which is a continuation of application No. 15/799,793, filed on Oct. 31, 2017, now Pat. No. 10,159,727, which is a continuation of application No. 15/639,632, filed on Jun. 30, 2017, now Pat. No. 9,849,167, which is a continuation of application No. 15/200,751, filed on Jul. 1, 2016, now Pat. No. 9,730,989.

(60) Provisional application No. 62/231,351, filed on Jul. 2, 2015.

(51) Int. Cl.
A61K 35/76    (2015.01)
A61K 39/12    (2006.01)
A61K 39/00    (2006.01)
C12N 5/0784    (2010.01)

(52) U.S. Cl.
CPC .......... *A61K 39/0011* (2013.01); *A61K 35/76* (2013.01); *A61K 39/12* (2013.01); *C12N 5/0639* (2013.01); *A61K 2039/5154* (2013.01); *A61K 2039/572* (2013.01); *A61K 2039/585* (2013.01); *C12N 2501/998* (2013.01); *C12N 2770/24132* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,048,686 A | 4/2000 | Lyday |
| 6,511,667 B1 | 1/2003 | Eckels et al. |
| 6,524,587 B1 | 2/2003 | Lyday |
| 7,217,418 B2 | 5/2007 | Eckels et al. |
| 8,415,152 B2 | 4/2013 | Muhlradt et al. |
| 8,889,118 B2 | 11/2014 | Okano et al. |
| 9,730,989 B2 | 8/2017 | Lyday |
| 9,849,167 B2 | 12/2017 | Lyday |
| 1,015,972 A1 | 12/2018 | Lyday |
| 1,035,755 A1 | 7/2019 | Lyday |
| 2002/0146396 A1 | 10/2002 | Albert et al. |
| 2007/0065467 A1 | 3/2007 | Krieg et al. |
| 2007/0082400 A1 | 4/2007 | Healey et al. |
| 2007/0087015 A1 | 4/2007 | Eckels et al. |
| 2013/0089567 A1 | 4/2013 | Whitehead et al. |
| 2013/0183343 A1 | 7/2013 | Czerniecki et al. |
| 2015/0166532 A1 | 6/2015 | Gray et al. |
| 2016/0058852 A1 | 3/2016 | Ter et al. |
| 2017/0087233 A1 | 3/2017 | Lyday |
| 2019/0298764 A1 | 10/2019 | Lyday |
| 2020/0078424 A1 | 3/2020 | Lyday |

FOREIGN PATENT DOCUMENTS

| | | |
|---|---|---|
| JP | 2004507445 A | 3/2004 |
| WO | WO-0057705 A1 | 10/2000 |
| WO | WO-0156599 A2 | 8/2001 |
| WO | WO-2008022196 A2 | 2/2008 |
| WO | WO-2012160199 A1 | 11/2012 |
| WO | WO-2013188315 A1 | 12/2013 |
| WO | WO-2016179475 A1 | 11/2016 |
| WO | WO-2017004567 A1 | 1/2017 |
| WO | WO-2017053873 A1 | 3/2017 |
| WO | WO-2018093907 A1 | 5/2018 |
| WO | WO-2018129202 A1 | 7/2018 |
| WO | WO-2018232166 A1 | 12/2018 |

OTHER PUBLICATIONS

Sondak et al. Allogeneic and autologous melanoma vaccines: where have we been and where are we going? Clin Cancer Res 12(7 Pt 2):2337s-2341s (2006).
U.S. Appl. No. 15/275,073 Office Action dated Aug. 30, 2019.
U.S. Appl. No. 15/275,073 Office Action dated Jan. 17, 2020.
U.S. Appl. No. 16/413,444 Office Action dated Aug. 19, 2019.
U.S. Appl. No. 16/413,444 Office Action dated Nov. 20, 2019.
Co-pending U.S. Appl. No. 16/714,370, filed Dec. 13, 2019.
"Lyday, et al., "Overcoming tumor immune evasion with an unique arbovirus", Journal of Translation Medicine (2015) 13:3 pp. 2-13".
Sarathy et al. Mouse models of dengue virus infection for vaccine testing. Vaccine 33(50):7051-7060 (2015).
Tan et al. Subcutaneous infection with non-mouse adapted Dengue virus D2Y98P strain induces systemic vascular leakage in AG129 mice. Ann Acad Med Singapore 40(12):523-532 (2011).
Andersen et al. Spontaneous immunity against Bcl-xL in cancer patients. J Immunol 175(4):2709-2714 (2005).

(Continued)

*Primary Examiner* — Stacy B Chen
(74) *Attorney, Agent, or Firm* — Wilson Sonsini Goodrich & Rosati

(57) ABSTRACT

Described herein are compositions and methods for treating cancer through the combination of tumor antigen-pulsed dendritic cells and Dengue Virus. The combination of the two forms of therapeutic intervention provides enhanced tumor cell reduction compared to either alone. The cancer targeted by compositions and methods described herein may be a solid cancer or blood cancer.

20 Claims, 3 Drawing Sheets

Specification includes a Sequence Listing.

(56) References Cited

OTHER PUBLICATIONS

Angarone. Epidemiology and Prevention of Viral Infections in Patients with Hematologic Malignancies. Infect Disord Drug Targets 11(1):27-33 (2011).
Angsubhakorn et al. Neurovirulence detection of dengue virus using rhesus and cynomolgus monkeys. J Virol Methods 18(1):13-24 (1987).
Anguille et al. Clinical use of dendritic cells for cancer therapy. Lancet Oncol 15:e257-267 (2014).
Anikeeva et al. Mechanisms Controlling Granule-mediated Cytolytic Activity of Cytotoxic T Lymphocytes. Immunol Res 51(2-3):183-194 (2011).
Armstrong et al. Efficiency of dengue serotype 2 virus strains to infect and disseminate in Aedes aegypti. Am J Trop Med Hyg 68:539-544 (2003).
Balmaseda et al. Serotype-Specific Differences in Clinical Manifestations of Dengue. Am J Trop Med Hyg 74(3):489-456 (2006).
Bente et al. Dengue Fever in Humanized NOD/SCID Mice. J Virol 79(21):13797-13799 (2005).
Bozza et al. Multiplex cytokine profile from dengue patients: MIP-1b and IFN-gamma as predictive factors for severity. BMC Infect Dis 8:86-93 (2008).
Cabrera et al. Analysis of HLA expression in human tumor tissues. Cancer Immunol Immunother 52:1-9 (2003).
Carreno et al. IL-12p70-producing patient DC vaccine elicits Tc1-polarized immunity. J Clin Invest 123(8):3383-3394 (2013).
Chakraborty et al. Emergence of regulatory CD4+ T cell responses to repetitive stimulation with antigen-presenting cells in vitro: implications in designing APC-based tumor vaccines. J Immunol 162:5576-5583 (1999).
Chalaem et al. Characterization of a Chikungunya virus strain isolated from banked patients' sera. Virol J 13(1):150 (2016).
Chang et al. Production of IL-1 by human monocytes exposed to dengue virus. J Infect Dis 170:811-817 (1994).
Chen et al. Activation of terminally differentiated human monocytes/macrophages by dengue virus: productive infection, hierarchical production of innate cytokines and chemokines, and the synergistic effect of lipopolysaccharide. J Virology 76:9877-9887 (2002).
Chiang et al. A dendritic cell vaccine pulsed with autologous hypochlorous acid-oxidized ovarian cancer lysate primes effective broad antitumor immunity: from bench to bedside. Clin Cancer Res 19(17):4801-4815 (2013).
Chiang et al. Optimizing parameters for clinical-scale production of high IL-12 secreting dendritic cells pulsed with oxidized whole tumor cell lysate. J Transl Med 14;9:198 (2011).
Crooks et al. The use of the Karnofsky Performance Scale in determining outcomes and risk in geriatric outpatients. J Gerontol 46:M139-M144 (1991).
De Haan et al. Measuring quality of life in stroke. Stroke 24:320-327 (1993).
Den Boer et al. Longevity of antigen presentation and activation status of APC are decisive factors in the balance between CTL Immunity Vs. Tolerance. J Immunol 167:2252-2258 (2001).
Dengue: Guidelines for Diagnosis, Treatment, Prevention and Control. World Health Organization (160 pgs) (2009).
Dequen et al. Systematic review and network meta-analysis of overall survival comparing 3 mg/kg Ipilimumab with alternative therapies in the management of pre-treated patients with unresectable Stage III or IV melanoma. Oncologist 17(11):1376-1385 (2012).
Diamond et al. Infection of human cells by dengue virus is modulated by different cell types and viral strains. J Virology 74(17):7814-7823 (2000).
Dillman et al. High-dose IL2 in metastatic melanoma: better survival in patients immunized with antigens from autologous tumor cell lines. Cancer Biother Radiopharm 29(2):53-57 (2014).
Dohnal et al. CD40 ligation restores type 1 polarizing capacity in TLR4-activated dendritic cells that have ceased interleukin-12 expression. J Cell Mol Med 13(8B):1741-1750 (2009).
Doyle et al. 9.1.1 Principles Governing the Use of Cancer Chemotherapy in Palliative Care. Oxford Textbook of Palliative Medicine, Oxford University Press. (p. 255) (1993).
Draghiciou et al. Therapeutic immunization and local low-dose tumor irradiation, a reinforcing combination. Int J Cancer 177(3):311-327 (2012).
Dudek et al. Inducers of Immunogenic Cancer Cell Death. Cytokine Growth Factor Rev 24(4):319-333 (2013).
Eckels et al. Isolation of a Temperature—Sensitive Dengue—2 Virus Under Conditions Suitable for Vaccine Development. Infect Immun 14(5):1221-1227 (1976).
Edelman et al. A live attenuated dengue-1 vaccine candidate (45AZ5) passaged in primary dog kidney cell culture is attenuated and immunogenic for humans. J Infect Dis. 170(6):1448-1455 (1994).
Ellem et al. The labyrinthine ways of cancer immunotherapy-T cell, tumor cell encounter: 'How do I lose thee? Let me count the ways'. Ad Cancer Res 75:203-249 (1998) .
Endy. Human immune responses to dengue virus infection: lessons learned from prospective cohort studies. Front Immunol 5:183 (2014).
Flavell et al. The polarization of immune cells in the tumour environment by TGFβ. Nat Rev Immunol 10(8):554-567 (2010).
Fracol et al. Response to HER-2 pulsed DC1 vaccines is predicted by both HER-2 and estrogen receptor expression in DCIS. Ann Surg Oncol 20(10):3233-3239 (2013).
Franciszkiewicz et al. CD103 or LFA-1 engagement at the immune synapse between cytotoxic T cells and tumor cells promotes maturation and regulates T-cell effector functions. Cancer Res 73(2):617-628 (2013).
Gabrilovitch et al. Dendritic cells in antitumor immune responses. II. Dendritic cells grown from bone marrow precursors, but not mature DC from tumor-bearing mice, are effective antigen carriers in the therapy of established tumors. Cell Immunol 70(1):111-119 (1996).
Ganss et al. Combination of T-cell therapy and trigger of inflammation induces remodeling of the vasculature and tumor eradication. Cancer Research 62:1462-1470 (2002).
Genevive et al. CD40-CD40 Ligand Interaction between Dendritic Cells and CD8+ T Cells Is Needed to Stimulate Maximal T Cell Responses in the Absence of CD4+ T Cell Help. J Immunol 178(5):2844-2852 (2007).
George et al. Chapter 5: Clinical spectrum of dengue infection. Dengue and Dengue Hemorrhagic Fever (Gubler and Kuno, CAB International) (25 pgs) (1997).
Gervais et al. In vitro antitumor lymphocyte generation using dendritic cells and innate immunity mechanisms as tumor cell treatments. Anticancer Res 27(4B):2385-2392 (2007).
Gottardis et al. Estradiol-stimulated growth of MCF-7 tumors implanted in athymic mice: a model to study the tumoristatic action of tamoxifen. J Steroid Biochem 30: 311-314 (1988).
Gupta et al. Acute disseminated encephalomyelitits associated with dengue infection, a case report with literature review. J Neurol Sci 335(1-2):216-218 (2013).
Habaragamuwa et al. N-acetylcystein in dengue-associated severe hepatitis. Indian J Crit Care Med 18(3):181-184 (2014).
Hahn et al. Nucleotide sequence of dengue 2 RNA and comparison of the encoded proteins with those of other flaviviruses. Virology 162:167-180 (1988).
Halstead. Etiologies of the Experimental Dengues of Siler and Simmons. Am J Trop Med Hys 23:974-982 (1974) (http://www.ajtmh.org/content/23/5/974.long).
Harris et al. Rapid subtyping of dengue viruses by restriction site-specific (RSS)-PCR. Virology 253:86-95 (1999).
Heylmann et al. Radiation sensitivity of human and murine peripheral blood lymphocytes, stem, and progenitor cells. Biochim Biophys Acta 1846(1):121-129 (2014).
Hober et al. High levels of sTNFR p75 and TNF alpha in dengue-infected patients. Microbiol Immunol 40:569-573 (1996).
Hollen et al. Measurement of quality of life in patients with lung cancer in multicenter trials of new therapies. Cancer 73:2087-2098 (1994).
Hung. Fluid Management for dengue in children. Paediatrics and Child Health 32(S-1):39-42 (2012).

(56) References Cited

OTHER PUBLICATIONS

Islas-Rodríguez et al. Effect of in vitro infection with dengue virus (DEN-2) on various cellular immune response functions in the mouse. Archivos de Investiga cion Medica 21(2):87-93 (1990) (English Abstract).
Janikashvili et al. Personalized dendritic cell-based tumor immunotherapy. Immunotherapy 2(1):57-68 (2010).
Jing et al. Combined immune checkpoint protein blockade and low dose whole body irradiation as immunotherapy for myeloma. J ImmunoTher Cancer 3(1):2 (15 pgs) (2015).
Kaka et al. Using Dendritic Cell Maturation and IL-12 Producing Capacity as Markers of Function: A Cautionary Tale. J Immunother 31(4):359-369 (2008).
Kawasaki et al. Toll-Like Receptor Signaling Pathways. Fron Immunol 5:461 (2014).
Kelley et al. Dengue Hemorrhagic Fever-Associated Immunomediators Induced via maturation of Dengue Virus Nonstructural 4B Protein in Monocytes Modulate Endothelial Cell Adhesion Molecules and Human Microvascular Endothelial Cells Permeability. Virology 422(2):326-337 (2012).
Khan et al. The Evolving Role of Radiation Therapy in the Management of Malignant Melanoma. Int J Radiat Oncol Biol Phys 80(3):645-654 (2011).
Kuo et al. Liver biochemical tests and dengue fever. Am J Trop Med Hyg 47:265-270 (1992).
Kurane et al. Activation of T lymphocytes in dengue virus infections. High levels of soluble interleukin 2 receptor, soluble CD4, soluble CD8, interleukin 2, and interferon-gamma in sera of children with dengue. J Clin Invest 88:1473-1480 (1991).
Kurane et al. Dengue virus infection of human skin fibroblasts in vitro production of IFN-Beta, IL-6, and GM-CSF. Arch Virol 124:21-30 (1992).
Kurlander et al. A functional comparison of mature human dendritic cells prepared in fluorinated ethylene-propylene bags or polystyrene flasks. Transfusion 46(9):1494-1504 (2006).
Kuss et a. Clinical significance of decreased zeta chain expression in peripheral blood lymphocytes of patients with head and neck cancer. Clin Cancer Res 5:329-334(1999).
Lambert et al. Intradermal vaccine delivery: will new delivery systems transform vaccine administration? Vaccine 26:3197-3208 (2008).
Lee et al. Acute myocarditis in dengue hemorrhagic fever: a case report and review of cardiac complications in dengue-affected patients. Int J Infect Dis 14:e919-e922 (2010).
Lee et al. Clinical characteristics, risk factors, and outcomes in adults experiencing DHF complicated with acute renal failure. Am J Trop Med Hyg 80(4): 651-655 (2009).
Leitmeyer et al. Dengue Virus structural changes that correlate with pathogenesis. J Virol 73:4738-4747 (1999).
Lesterhaus et al. Dendritic Cell vaccines in melanoma: from promise to proof? Crit Rev Oncol Hematol 66(2):118-134 (2008).
Linette et al. Cardiovascular toxicity and titin cross-reactivity of affinity-enhanced T cells in myeloma and melanoma. Blood 122(6):863-871 (2013).
Lizarraga et al. Dengue-associated kidney disease. J Nephropathol 3(2):57-62 (2014).
Lum et al. Dengue-associated adult respiratory distress syndrome. Ann Trop Paediatr 15(4):335-339 (1995).
Lutz et al. An advanced culture method for generating large quantities of highly pure dendritic cells from mouse bone marrow. J Immunol Methods 223:77-92 (1999).
Lövgren et al. Enhanced stimulation of human tumor-specific T cells by dendritic cells matured in the presence of interferon-γ and multiple toll-like receptor agonists. Cancer Immunol Immunother 66(10):1333-1344 (2017).
Lyday et al. Overcoming tumor immune evasion with an unique arbovirus. J Transl Med 13:3 (2015) (12 pgs).
Ma et al. The TLR7 agonists imiquimod and gardiquimod improve DC-based immunotherapy for melanoma in mice. Cell Mol Immunol 7(5):381-388 (2010).
MACS@ GMP Cell Differentiation Bag. Miltenyi Biotec Product Insert. Issued: Aug. 2012 (2 pgs).
Malavige et al. T cell responses in dengue viral infections. J Clin Virol 58(4):605-611 (2013).
Malik et al. Dengue encephalopathy-still and enigma? J Infect Dev Ctries 8(8):1076-1078 (2014).
Markiewicz et al. IL-12 enhances CTL synapse formation and induces self-reactivity. J Immunol 182(3)1 351-1361 (2009).
Matthew et al. Dominant recognition by human CD8+ CTL of dengue virus non-structural proteins NS3 and NS1.2a. J Clin Invest 98:1684-1691 (1996).
McKee et al. Lack of attenuation of a candidate Dengue-1 vaccine (45AZ5), in human volunteers. Am J Trop Med Hyg Mar 36:435-442 (1987).
Media for Multiplitoplasma Viroids Is Not Rare—Causative Agent (available at https://www.alpfmedical.info/causative-agent/i-ptg.html) ALPF Medical Research (5 pgs) (updated Jul. 21, 2017) .
Mettler et al. Virus Inoculation in Mice Bearing Ehrlich Ascitic Tumors: Antigen Prouction and Tumor Regression. Infect Immun 37(1):23-27 (1982).
Mittendorf et al. Final report of the phase I/II clinical trial of the E75 (nelipepimut-S) vaccine with booster inoculations to prevent disease recurrence in high-risk breast cancer patients. Ann Oncol 25(9):1735-1742 (2014).
Mizoguchi et al. Alterations in signal transduction molecules in T lymphocytes from tumor-bearing mice. Science 258:1795-1798 (1992).
Morse et al. Migration of human DC after injection in Patients with Metastatic Malignancies. Cancer Res 59:56-58 (1999).
Nakai et al. Immunoregulatory T cells in the peripheral blood of melanoma patients treated with melanoma antigen-pulsed dendritic cell vaccination. J Dermatol Sci 54:31-37 (2009).
Napolitani et al. Selected Toll-like receptor agonist combinations synergistically trigger a T helper type 1-polarizing program in dendritic cells. Nat Immunol 6(8):769-776 (2005).
Nava et al. An optimized method for manufacturing a clinical-scale Dendritic Cell-based vaccine for the treatment of Glioblastoma. PLoS One 7(12):e52301 (2012).
Nielsen. The Relationship of intersecting immunological components in Dengue pathogenesis. Virol J 6:1-7 (2009).
Nocera et al. Restoring Lost Anti-HER-2 Th1 Immunity in Breast Cancer: A Crucial Role for Th1 Cytokines in Therapy and Prevention. Front Pharmacol 7:356 (2016).
Nunes et al. Emergence and potential for spread of Chikungunya virus in Brazil. BMC Medicine 13:102 (2015).
Oken et al. Toxicity and Response Criteria of The Eastern Cooperative Oncology Group. Am J Clin Oncol 5:649-655 (1982).
Oleinika et al. Suppression, subversion, and escape: the role of regulatory T cells in cancer progression. Clin Exp Immunol 171:36-45 (2012).
Olszanski. Current and Future Roles of Targeted Therapy and Immunotherapy in Advanced Melanoma. J Manag Care Pharm 20(4):346-354 (2014).
Osborne et al. Effects of estrogens and antiestrogens on growth of human breast cancer cells in athymic nude mice. Cancer Res 45:584-590 (1985).
O'Toole et al. Evaluating cancer patients for rehabilitation potential. West J Med 155:384-387 (1991).
Park et al. Radiation-induced vascular damage in tumors: implications of vascular damage in ablative hypofractionated radiotherapy (SBRT and SRS). Radiat Res 177(3):311-327 (2012).
Pasca et al. Role of Interleukin-12 in patients with dengue hemorrhagic fever. FEMS Immunol Med Microbiol 28:151-155 (2000).
Paustian et al. Effect of multiple activation stimuli on the generation of Th1-polarizing dendritic cells. Hum Immuon 71(1):24-31 (2011).
PCT/US2016/040787 International Preliminary Report on Patentability dated Jan. 11, 2018.
PCT/US2016/040787 International Search Report and Written Opinion dated Sep. 22, 2016.
PCT/US2016/053554 International Preliminary Report on Patentability dated Apr. 5, 2018.
PCT/US2016/053554 International Search Report and Written Opinion dated Feb. 3, 2017.

(56) References Cited

OTHER PUBLICATIONS

PCT/US2016/053554 Invitation to Pay Additional Fees dated Nov. 28, 2016.
PCT/US2017/061810 International Search Report and Written Opinion dated Mar. 15, 2018.
PCT/US2017/061810 Invitation to Pay Additional Fees dated Jan. 22, 2018.
PCT/US2018/012408 International Search Report and Written Opinion dated Mar. 29, 2018.
PCT/US2018/037616 International Search Report and Written Opinion dated Nov. 29, 2018.
Pfeiffer. Dissertation—Generation of effective designer dendritic cells for therapeutic cancer vaccination using RNA electroporation. The Faculty of Science, University of Erlangen—Nuremberg (146 pgs) (2013) (w/English translation).
Prestwich et al. The case of oncolytic viruses versus the immune system: waiting on the judgment of Solomon. Hum Gene Ther 20(10):1119-1132 (2009).
Quatromonie et al. The timing of TGF-β inhibition affects the generation of antigen-specific CD8+ T cells. BMC Immunol 14:30 (2013).
Rajat et al. Unusual manifestations in dengue outbreak 2009, Delhi, India. J Communicable Dis 42(4):255-261 (2010).
Rigau-Perez et al. Dengue activity in Puerto Rico, 1990. Puerto Rico Health Science Journal 11(2):65-68 (1992).
Rouas et al. Dendritic cells generated in clinical grade bags strongly differ in immune functionality when compared with classical DCs generated in plates. J Immunother 33(4):352-363 (2010).
Santos et al. Dendritic Cell-Based Cancer Vaccines. J Immunol 200(2):443-449 (2018).
Schag et al. Karnofsky performance status revisited: Reliability, validity,and guidelines. J Clin Oncol 2:187-193 (1984).
Sharma et al. Guillain-Barre syndrome occurring during dengue fever. J Indian Med Assoc 109(9):675 and 682 (2011).
Sheikh et al. Sipuleucel-T immune parameters correlate with survival: an analysis of the randomized phase 3 clinical trials in men with castration-resistant prostate cancer. Cancer Immunol Immunother 62(1):137-147 (2013).
Shresta et al. Critical roles for both STAT1-dependent and STAT1-independent pathways in the control of primary dengue virus infection in mice. J Immunol 175:3946-3954 (2005).
Singhi et al. Dengue and Dengue Hemorrhagic Fever: management issues in an intensive care unit. J Pediatr (Rio J) 83(Supp 2):S22-S35 (2007).
Sinkovics et al. New Developments in the Virus Therapy of Cancer: A Historical Review. Intervirology 36:193-214 (1993).
Sorlie et al. Gene expression patterns of breast carcinomas distinguish tumor subclasses with clinical implications. PNAS USA 98:10869-10874 (2001).
Stanton et al. Clinical significance of tumor-infiltrating lymphocytes in breast cancer. J Immunother Cancer 4:59 (2016).
Straussman et al. Tumour micro-environment elicits innate resistance to RAF inhibitors through HGF secretion. Nature 487:500-504 (2012).
Taweechaisupapong et al. Langerhans cell density and serological changes following intradermal immunisation of mice with dengue 2 virus. J Med Microbiol 45:138-145 (1996).
Turcotte et al. Immunotherapy for metastatic solid cancers. Adv Surg 45:341-360 (2011).
Turnis et al. Enhancement of dendritic cells as vaccines for cancer. Immunotherapy 2(6):847-862 (2010).
U.S. Appl. No. 15/200,751 Office Action dated Feb. 7, 2017.
U.S. Appl. No. 15/275,073 Office Action dated Aug. 15, 2018.
U.S. Appl. No. 15/275,073 Office Action dated Jan. 28, 2019.
U.S. Appl. No. 15/275,073 Office Action dated Jul. 14, 2017.
U.S. Appl. No. 15/275,073 Office Action dated Mar. 31, 2017.
U.S. Appl. No. 15/639,632 Office Action dated Aug. 3, 2017.
U.S. Appl. No. 15/799,793 Office Action dated Dec. 13, 2017.
U.S. Appl. No. 15/799,793 Office Action dated May 25, 2018.
U.S. Appl. No. 16/172,487 Office Action dated Dec. 14, 2018.
Valerio et al. Hemorrhagic exanthema due to dengue virus induced by Acetylsalicylic acid. An Sist Sancit Navar 29(3):439-442 (2006).
Van Mierlo et al. Activation of dendritic cells that cross-present tumor-derived antigen licenses CD8+ CTL to cause tumor destruction. J Immunol 173:6753-6759 (2004).
Vaughn et al. Dengue viremia titer, Antibody Response Pattern, and Virus Serotype Correlate with Disease Sensitivity. J Infect Dis 181:2-9 (2000).
Verdijik et al. Limited amounts of DC migrate into the T-cell area of lymph nodes, but have high immune activating potential in melanoma patients. Clin Can Res 15(7):2531-2540 (2009).
Via et al. IL-12 stimulates the development of acute graft-versus-host disease in mice that normally would develop chronic, autoimmune graft-versus-host disease. J Immunol 153(9):4040-4047 (1994).
Wahid et al. A comparison of the pattern of liver involvement in Dengue Hemorrhagic Fever with classic Dengue Fever. Southeast Asian J Trop Med Public Health 31(2):259-263 (2000).
Wolchok et al. Guidelines for the evaluation of immune therapy activity in solid tumors: immune-related response criteria. Clin Cancer Res 15(23):7412-7420 (2009).
Wolchok et al. Nivolumab plus ipilimumab in advanced melanoma. N Eng J Med. 369:122-133(2013).
Wu et al. Human skin Langerhans cells are targets of dengue virus infection. Nature Medicine 6:816-820 (2000).
Xu et al. High-avidity antitumor T-cell generation by toll receptor 8-primed, myeloid-derived dendritic cells is mediated by IL-12 production. Surgery 140(2):170-178 (2006).
Yang et al. TGF-beta and immune cells: an important regulatory axis in the tumor microenvironment and progression. Trends Immunol 31(6):220-227 (2010).
Yeo et al. Lack of clinical manifestations in asymptomatic dengue infection is attributed to broad down-regulation and selective up-regulation of host defence response genes. PloS One 9(4):e92240 (2014).
Yu et al. New Immunotherapy Strategies in Breast Cancer. Int J Environ Res Public Health 14(1):pii:68 (2017).
Zellweger et al. Mouse models to study dengue virus immunology and pathogenesis. Front Imunol 10(5):151 (Apr. 2014).
Zitvogel et al. Therapy of murine tumors with tumor-peptide-pulsed dendritic cells: dependence on T cells, B7 costimulation, and T-helper cell-1 associated cytokines. J Exp Med 183:87-97 (1996).
Zobywalski et al. Generation of clinical grade dendritic cells with capacity to produce biologically active IL-12p70. J Transl Med 5:18 (2007).
Lyday, et al., "Triad Immunologies, LLC, Presents: Hyperthermia + Cytokine Cascade Dendritic Cell Vaccine for Solid Tumors" Slides published May 1, 2011, pp. 1-40.

```
                         SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Gly Ser Arg Asn Gln Asp Trp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ala Tyr Arg Tyr His Leu Leu
1               5

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcccaag aagggccat                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcagctcca tagattgct                                              19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgttgctg cagatggaa                                              19

<210> SEQ ID NO 6
<211> LENGTH: 19
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 6
gtgtcacaga cagtgaggt                                               19

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ile Ile Asn Phe Glu Lys Leu
1               5
```

COMPOSITIONS AND METHODS FOR COMBINATION THERAPY WITH DENGUE VIRUS AND DENDRITIC CELLS

CROSS-REFERENCE

This application is a Continuation of U.S. patent application Ser. No. 16/172,487, filed Oct. 26, 2018, which is a Continuation of U.S. patent application Ser. No. 15/799,793, filed Oct. 31, 2017, which is a Continuation of U.S. patent application Ser. No. 15/639,632, filed Jun. 30, 2017, now U.S. Pat. No. 9,849,167, which is a Continuation of U.S. patent application Ser. No. 15/200,751, filed Jul. 1, 2016, now U.S. Pat. No. 9,730,989, which claims the benefit of U.S. Provisional Application No. 62/231,351, filed Jul. 2, 2015, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 29, 2016, is named 48253-702_304_SL.txt and is 1,871 bytes in size.

BRIEF SUMMARY

Provided herein are methods for treating cancer in a subject in need thereof, comprising: incubating dendritic cells (DCs) with at least one tumor cell antigen; administering a Dengue Virus Type 2 serotype strain DENV-2 #1710 to the subject; and administering the DCs to the subject. Further provided herein are methods, wherein the at least one tumor cell antigen is from a solid cancer cell or a blood cancer cell from the subject. Further provided herein are methods, wherein the blood cancer is leukemia or lymphoma. Further provided herein are methods, wherein the solid cancer is melanoma, breast, prostate, or brain cancer. Further provided herein are methods, wherein the DCs are collected by leukapheresis. Further provided herein are methods, wherein the DCs or the at least one tumor cell antigen are from the subject. Further provided herein are methods, wherein the DCs and the at least one tumor cell antigen are from the subject. Further provided herein are methods, wherein the at least one tumor cell antigen is from the subject. Further provided herein are methods, wherein the DCs and the at least one tumor cell antigen are from the subject. Further provided herein are methods, wherein the at least one tumor cell antigen is present in a suspension comprising single cells. Further provided herein are methods, wherein the DCs are pulsed with the at least one tumor cell antigen. Further provided herein are methods, wherein the at least one tumor cells antigen is a peptide. Further provided herein are methods, wherein the peptide is about 9 amino acids in length. Further provided herein are methods, wherein the Dengue Virus Type 2 serotype strain DENV-2 #1710 is present in an amount sufficient to induce a systemic infection. Further provided herein are methods, wherein the DCs are administered after the subject's temperature reaches 38 degrees Celsius or higher. Further provided herein are methods, wherein the DCs are administered after the subject's temperature reaches 38.5 degrees Celsius. Further provided herein are methods, wherein monocytes of the subject are processed obtain the DCs. Further provided herein are methods, wherein the DCs are mature DCs capable of antigen uptake.

Provided herein are methods for treating cancer in a subject in need thereof, comprising: lysing tumor tissue from a subject to form a lysis product comprising apoptotic or necrotic bodies; incubating dendritic cells (DCs) with the lysis product; administering a Dengue Virus to a subject; and administering the DCs to the subject after the subject's temperature reaches 38 degrees Celsius or higher. Further provided herein are methods, wherein the tumor tissue comprises a cell from a solid cancer or a blood cancer. Further provided herein are methods, wherein the blood cancer is leukemia or lymphoma. Further provided herein are methods, wherein the solid cancer is melanoma, breast, prostate, or brain cancer. Further provided herein are methods, wherein the DCs are from the subject. Further provided herein are methods, wherein the DCs are collected by leukapheresis. Further provided herein are methods, wherein the DCs are not from the subject. Further provided herein are methods, wherein the tumor tissue is present in a suspension comprising single cells prior to lysis. Further provided herein are methods, wherein the DCs are pulsed with the lysis product. Further provided herein are methods, wherein the Dengue Virus is administered in an amount sufficient to induce a systemic infection. Further provided herein are methods, wherein obtaining DCs comprises processing the subject's monocytes to produce the dendritic cells. Further provided herein are methods, wherein the DCs are mature DCs capable of antigen uptake. Further provided herein are methods, wherein the tumor tissue is in an amount of 0.5 to 5 grams. Further provided herein are methods, wherein the tumor tissue is in an amount of 1 to 2 grams. Further provided herein are methods, wherein the Dengue Virus is serotype 1, 2, 3, 4, or 5. Further provided herein are methods, wherein the Dengue Virus is serotype 2. Further provided herein are methods, wherein the Dengue Virus is Dengue Virus Type 2 serotype strain DENV-2 #1710. Further provided herein are methods, wherein the Dengue Virus is present in an amount sufficient to induce a systemic infection. Further provided herein are methods, wherein the DCs are mature DCs capable of antigen uptake. Further provided herein are methods, wherein the DCs are administered to the subject after the subject's temperature reaches 38.5 degrees Celsius.

Provided herein are methods for targeting cancer cells, comprising: incubating dendritic cells (DCs) with at least one tumor cell antigen; administering a Dengue Virus Type 2 serotype strain DENV-2 #1710 to a subject; and administering the DCs to the subject.

Provided herein are methods for targeting cancer cells, comprising: lysing tumor tissue from a subject to form a lysis product comprising apoptotic or necrotic bodies; incubating dendritic cells (DCs) with the lysis product; administering a Dengue Virus to the subject; and administering the DCs to the subject after the subject's temperature reaches 38.5 degrees Celsius or higher.

Provided herein are compositions for reduction of tumor cells, the composition comprising an effective amount of Dengue Virus Type 2 serotype strain DENV-2 #1710 for initiating an immune response, wherein the Dengue Virus Type 2 serotype strain DENV-2 #1710 provides for an enhanced reduction of tumor cells when administered prior to administration of tumor antigen-primed dendritic cells compared to administration of either agent alone. Further provided herein are compositions, wherein the tumor cells are from a solid cancer or a blood cancer. Further provided herein are compositions, wherein the blood cancer is leukemia or lymphoma. Further provided herein are compositions, wherein the solid cancer is melanoma, breast, prostate, or brain cancer.

Provided herein is use of an effective amount of Dengue Virus Type 2 serotype strain DENV-2 #1710 for the manufacture of a medicament for the treatment of cancer. Provided herein is use of an effective amount of Dengue Virus Type 2 serotype strain DENV-2 #1710 for treating cancer. Provided herein is An effective amount of Dengue Virus Type 2 serotype strain DENV-2 #1710 for use in treating of cancer.

BACKGROUND

Immunotherapy, unlike cytotoxic drugs, radiation, and surgery, stimulates the immune system to recognize and kill tumor cells. Numerous attempts have been made in stimulating the immune system to recognize and destroy tumor cells. These have been met with limited success due to the self-identity of peptides selected as target for immunotherapy, lack of immune activation, adverse events, and/or tumor immune evasion mechanisms.

DETAILED DESCRIPTION OF INVENTION

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term "subject" as used herein includes to mammals. Mammals include rats, mice, non-human primates, and primates, including humans.

Combination Delivery

Figure 1:
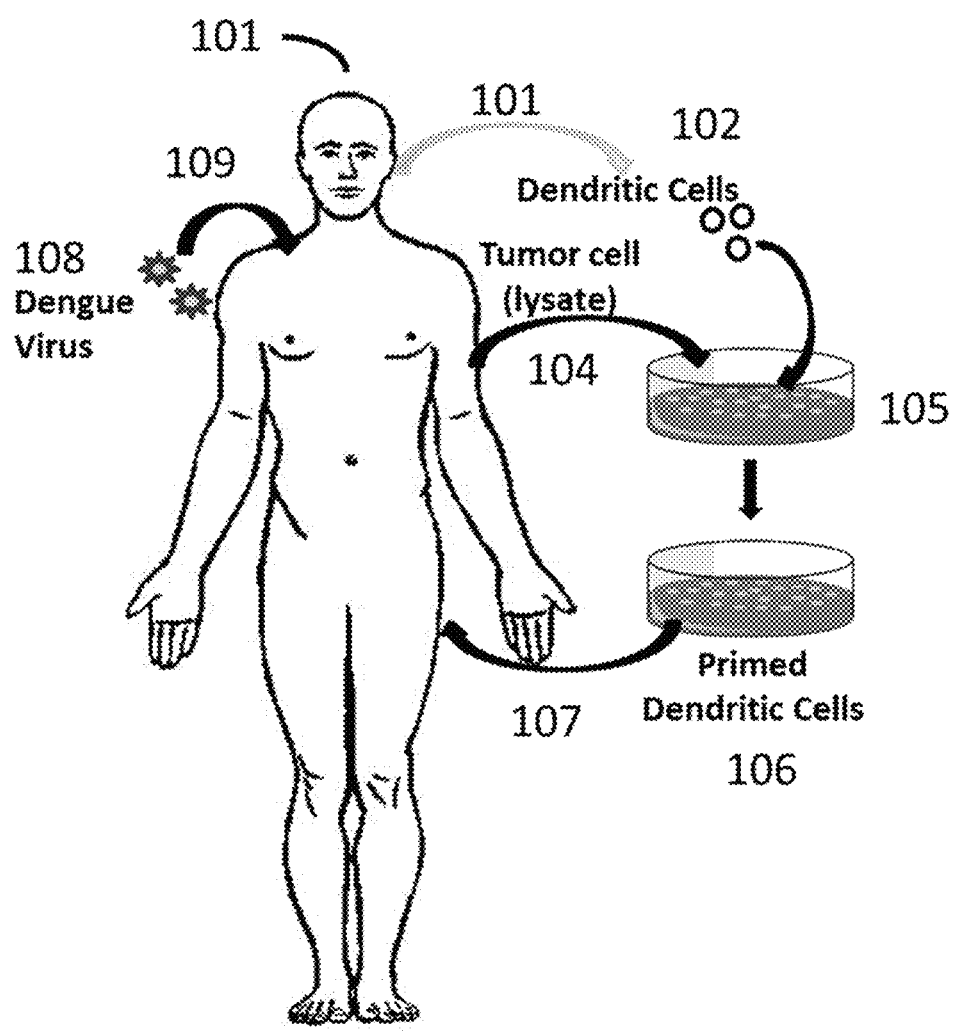
FIG. 1 exemplifies a method of treatment with Dengue virus and primed dendritic cells.

Described herein are compositions and methods wherein dendritic cell vaccination is combined with an adjuvant effect of a strain of Dengue virus (DV) to overcome tumor immune evasion mechanisms and deplete tumor cells. Methods described here may be used to treat a subject 101 for cancer by obtaining 101 dendritic cells 102 and tumor cells 104 from the subject, exposing the dendritic cells to the tumor cells or tumor cell lysate 105, also referred to as "pulsing" the dendritic cells, to primed (or "activated") the dendritic cells, delivering 107 the resulting primed and tumor-targeting dendritic cells to the subject after the subject has had his/her immune system stimulated with DV 108 (see, e.g., FIG. 1). Optionally, the tumor antigen is not from the subject can be used for pulsing the dendritic cells.

Tumor immune evasion mechanisms are responsible for the lack of efficacy seen with most immunotherapy platforms. Compositions and methods described herein provide for a multi-pronged approach, combining physiological (hyperthermic reduction of tumor perfusion), immunological (activation of effector cells of the adaptive and innate immune system), and apoptosis-inducing pathways (sTRAIL) to destroy tumor cells. Using DV as an adjuvant to activate many pathways working in synergy may support the eradication of mutated tumor cells, improving the clinical efficacy of the cancer immunotherapy. Methods described herein provide cancer immunotherapies based on multiple mechanisms of action in concert and result in a decline in the ability of the tumor cells to employ resistance methods compared to delivery of any single method along.

Disclosed herein are methods for treating cancer in a subject in need thereof, comprising: obtaining dendritic cells (DCs); incubating the DCs with at least one tumor cell antigen; administering a Dengue Virus Type 2 serotype strain to the subject; and administering the DCs to the subject. In some instances, the Dengue Virus Type 2 serotype strain is DENV-2 #1710. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate.

Methods of Isolating and Lysing Tumor Cells

Provided herein are methods for combination therapy with a DV and activated DCs to target tumor cells. In some instances, DCs are primed with tumor cells from a subject. In some instances, the tumor cells are isolated cells from a tumor microenvironment of the subject, referred to herein as tumor supporting cells. In some instances, dendritic cells are exposed to/pulsed with tumor cells, tumor supporting cells and/or peptides thereof, such that the dendritic cells will target tumor cells and/or tumor supporting cells that support tumor growth and metastasis (e.g. endothelial cells, vascular cells, immune cells, etc.). In some instances, peptides/antigens from tumor cells and tumor supporting cells induce dendritic cells or cytotoxic lymphocytes with receptors for peptides/antigens on both tumor cells and tumor supporting cells, resulting in targeting of the dendritic cells or cytotoxic lymphocytes to the tumor microenvironment rather than only the tumor cells. In some instances, tumor cells and/or tumor supporting cells are obtained from a biopsy of tumor tissue. In some instances, the biopsy comprises cells selected from tumor cells, adipocytes, fibroblasts, endothelial cells, infiltrating immune cells, and combinations thereof.

Provided herein are methods for combination therapy with a DV and activated DCs to target tumor cells, wherein the DCs are activated with lysed tumor cells and/or tumor supporting cells and surrounding extracellular matrix. In some instances, lysing comprises contacting the tumor cells and/or tumor supporting cells with an $NH_4Cl$ enzyme solution to eliminate red blood cells. In some instances, the lysing comprises contacting the tumor cells and/or tumor supporting cells with hypochlorous acid solution to induce immunogenic cell death. In some instances, the cells are lysed gently enough to not destroy peptides. In some instances, the cells are lysed to produce apoptotic or necrotic bodies. In some instances, the methods comprise lysing the tumor cells and/or tumor supporting cells with an enzymatic solution. In some instances, the methods comprise lysing the tumor cells and/or tumor supporting cells with a peroxide-free solution or a low peroxide-containing solution. In some instances, the methods comprise lysing the tumor cells and/or tumor supporting cells with a detergent solution. In some instances, the detergent is selected from, but is not limited to, Triton X-100, Triton X-114, NP-40, Brij-35, Brij-58, Tween 20, Tween 80, octyl glucoside, octyl thioglucoside, SDS, CHAPS, and CHAPSO. In some instances, the detergent solution is purified of peroxides, and other impurities. In some instances, the detergent is about 0.1% to about 10% v/v of the detergent solution. In some instances, the detergent is about 0.1% to about 5% v/v of the detergent solution. In some instances, the detergent is about 0.5% to about 5% v/v of the detergent solution. In some instances, the detergent is about 1% to about 10% v/v of the detergent solution. In some instances, the detergent is about 1% to about 5% v/v of the detergent solution. In some instances, the methods comprise lysing cells without shaking, vortexing, freezing, thawing, shear pressure, sonicating and/or heating the cells.

Methods of Isolating and Priming Dendritic Cells (DCs)

Provided herein are methods for combination therapy with a DV and activated DCs to target tumor cells, wherein the DCs comprise allogeneic or autologous dendritic cells. In some instances, methods described herein comprise administering allogeneic primed dendritic cells to a subject. In some instances, methods described herein comprise administering autologous primed dendritic cells to a subject. In some instances, methods described herein comprise obtaining dendritic cells from $CD34^+$ progenitor cells in the bone marrow. In some instances, methods described herein comprise obtaining dendritic cells from $CD1^+ CD14^+$ immature monocytes in the peripheral blood. In some instances, obtaining the dendritic cells comprises leukapheresis. In some instances, leukapheresis comprises withdrawing a unit of blood from the subject or a donor, separating a series of blood-components: red cells, platelets, and most of the plasma factors, which are returned to the subject, with the white blood cells remaining. In some instances, methods described herein comprise testing the white blood cells for sterility, shipping or storing them cold (4° C.), and or processing the DC from the apheresis product.

In some instances, methods described herein comprise pulsing DCs with a peptide. In some instances, the methods comprise pulsing DCs with a peptide that binds MEW Class I molecules ("MEW Class I peptide"). In some instances, methods described herein comprise pulsing DCs with a peptide that binds MHC Class II molecules ("MHC Class II peptides"). In some instances, methods described herein comprise pulsing DCs with MEW Class I peptides and MEW Class II peptides. In some instances, the pulsing makes the DCs competent to prime CTL and target CTL to tumors. In some instances, methods described here comprise pulsing DCs with manufactured/synthetic Class I and/or Class II peptides. In some instances, the Class I and/or class II peptides are manufactured, then added to the DC medium, optionally in microgram quantities or less. In some instances, methods described herein include Class II peptides for a sustained immune response. In some instances, methods described herein comprise DNA or RNA sequencing of the peptide (i.e. tumor antigen) and/or using electroporation to insert the DNA or RNA into the DC to trigger antigen processing. In some instances, methods described herein do not require HLA matching of DCs. In some instances, the peptide or portion thereof is represented by an amino acid sequence selected from EGSRNQDWL (SEQ ID NO:1), (TAYRYHLL) (SEQ ID NO: 2), or combinations thereof.

In some instances, methods described herein comprise contacting the dendritic cells with autologous tumor cells or lysates thereof. In some instances, methods described herein comprise contacting the dendritic cells with autologous whole-tumor cells (e.g. tumor cells and tumor supporting cells) or lysates thereof which contain the full array of potential antigens for a broad and deep immune response. In some instances, methods described herein comprise contacting the dendritic cells with tumor cell lysate comprising apoptotic or necrotic bodies. In further instances, the tumor cell lysate comprises tumor antigens from the microenvironment surrounding the tumor cells, such as extracellular matrix proteins. In some instances, contacting comprises pulsing, wherein pulsing comprises contacting the dendritic cells more than once at one or more intervals. In some instances, "pulsing" of DCs comprises contacted DCs with peptides/antigens, tumor cells, tumor supporting cells, tumor cell lysate and/or tumor supporting cell lysate. In some instances, lysing the tumor cells does not comprise trypsin enzyme digestion and freeze-thaw cycles, which are simple and fast, but can damage the delicate peptides within. In some instances, methods described herein comprise using an automated cell processor, like the Miltenyi GentleMACS system, by way of non-limiting example, to manually mince the sample; suspend cells in PBS solution; and/or separate the tumor cells with a pre-selected tissue-specific software-controlled rotor system. In some instances, the single-cell suspension is membrane-lysed with minimal damage to tumor peptides. In some instances, methods described herein comprise pulsing the DCs from about 1 hour to about 24 hours. In some instances, methods described herein comprise pulsing the DCs from about 12 hours to about 48 hours. In some instances, methods described herein comprise pulsing the DCs from about 8 hours to about 24 hours. In some instances, methods described herein comprise pulsing the DCs for about 18 hours.

Dengue Viruses

Provided herein are methods for combination therapy with a Dengue virus (DV) and activated DCs to target tumor cells, wherein the DV is administered to a subject. As used herein, the term "Dengue virus" includes any serotype of Dengue virus serotypes 1, 2, 3, 4, or 5.

Dengue viruses are Arboviruses, and are transmitted exclusively by mosquitoes of the *Aedes aegypti* and *albopictus* species. The virus has a complex life cycle involving an unidentified forest-dwelling mammalian reservoir (possibly primates), and human hosts. The female mosquito takes a blood meal from an infected person, the virus replicates to a high infectious titer (105/ml), in gut epithelial cells, then is transmitted to another person when the mosquito withdraws its stylet using back pressure after another blood meal. Dengue epidemics infect 50 million persons annually, with several thousand deaths, usually children with inadequate treatment of secondary infection-related shock.

The Dengue virus genome encodes structural proteins, capsid protein C, membrane protein M, envelope protein E, and nonstructural proteins, NS1, NS2a, NS2b, NS3, NS4a, NS4b and NS5. In some instances, the Dengue virus is a live strain of the Dengue virus. In some instances, the Dengue virus is an attenuated strain of the Dengue virus. In some instances, the Dengue virus is a weakened strain of the Dengue virus. In some instances, the Dengue virus is selected the following serotypes of dengue virus: DENV-1, DENV-2, DENV-3, DENV-4, and DENV-5, and combinations thereof.

Dengue Viruses are positive-strand RNA viruses of the Togavirus Family, sub-family Flaviviridae, (Group B). The virus has an icoashederal geometry and is approximately 40-45 nanometers in diameter. The 11,000 base genome codes for a nucleocapsid (NC), protein, a prM membrane fusion protein, an envelope glycoprotein I, and 5 nonstructural proteins NS1-NS5. The NC protein forms the viral core, with the envelope spikes attached via the prM complex. The E glycoprotein is the main target of neutralizing antibodies, and the NS-3 and NS-4 proteins make up the main targets for CD4+ and CD8+CTL.

The dengue viruses make up five distinct serotypes, DENV-1 through DENV-5. The serotypes 2 and 4 are cross-neutralizing for IgG, and types 1 and 3 are also cross-neutralizing. Immunity is not complete, however, and dengue is unique among viral infections in that a subsequent infection by a non-cross-neutralizing serotype carries an increased risk of mortality due to shock syndrome from immune hyper-activation.

Provided herein are compositions and method using such compositions, wherein the composition comprises Dengue virus serotype 1, 2, 3, 4, or 5. In some instances, the DV is serotype 2. In some instances the DV serotype 2 is DENV-2 strain #1710. The strain is from a sample taken from Puerto Rico in 1985 and characterized as type A from a restriction site specific RT-PCR analysis using 4 primers (see Table 1) specific to the envelope gene region. See Harris et al., Virology 253, 86-95 (1999). Restriction site specific RT-PCR with these primers produces amplification products of 582 base pairs, 754 base pairs, and possibly 676 base pairs. The DENV-2 strain #1710 is recorded in a CDC database as entry number 555. See Harris (1999). The DENV-2 strain #1710 was isolated during a Puerto Rican epidemic. This outbreak had 9,540 suspected cases of DV, with one suspected, but no confirmed deaths due to the virus, which indicates the toxicity of DEN-2 strain #1710 is very low and therefore suitable for the methods disclosed herein.

TABLE 1

Sequence and Position of Primers to Amplify DENV-2 viruses

| Primer | Sequence | Genome Position | Strand |
|---|---|---|---|
| RSS1 | 5'-GGATCCCAAGAAGGGGCCAT-3' (SEQ ID NO: 3) | 1696-1715 | + |
| RSS2 | 5'-GGCAGCTCCATAGATTGCT-3 (SEQ ID NO: 4) | 2277-2259 | - |
| RSS3 | 5'-GGTGTTGCTGCAGATGGAA-3' (SEQ ID NO: 5) | 1524-1542 | + |
| RSS4 | 5'-GTGTCACAGACAGTGAGGT-3' (SEQ ID NO: 6) | 2371-2353 | - |

DV has many characteristics supporting its use as a potent immune-stimulant in cancer immunotherapy. DV has affinity for immature B-lymphocytes and antigen-presenting cells (APC) of monocyte/macrophage and DC lineage. A unique feature of DV is that primary infections result in activation of a $T_H1$-type response of CD4+ and CD8+ helper-inducer and cytotoxic-effector CTL. By infecting, but not killing the APC, DV up-regulates their CD80 and CD83 expression, resulting in a pro-inflammatory $T_H1$ cytokine profile. Primary DV infections induce a $T_H1$ type response with activated $CD4^+$ and $CD8^+$ effector T cells as well as LAK cells. This type of response is seen in patients having complete responses to cancer immunotherapies (see Table 2).

TABLE 2

Tumor immune evasion mechanisms and DV infection

| Immune evasion | Dengue counter-attack |
|---|---|
| Low levels of MHC on tumor cell prevent CTL recognition | Hi Interferon-γ raises MHC levels by up-regulating MHC gene expression |
| Point mutations in Tumor Peptides prevent TCR binding | LAK/CIK cells target "escaped" tumor cells expressing aberrant peptides or MHC |
| Tumor vessels lack factors for CTL attachment and trafficking | Hi [TNF-α] restores gaps by altering PECAM-1, restores ICAM-1/VCAM-1 expression and P and E-selectins |
| FasL can kill $Fas^+$ CTL by triggering apoptosis | Hi [IL-6, 15] protects $Fas^+$ CTL by up-regulating FLIP ligand |
| HLA-G protects from NK Cells | Hi [IL-2, 7, 12, 15] raise activation of NK |
| Stromal barriers inhibit CTL | Hi [IFN-γ] activates Macrophages to $M_1$ |
| Myeloid-Derived Suppressor Cells, (MDSC) | iNKT Cells can decrease MDSC |

TABLE 2-continued Tumor immune evasion mechanisms and DV infection

| Immune evasion | Dengue counter-attack |
|---|---|
| CTL inactivated by TGF-β | $T_H1$ cytokines reactivate tolerant CTL |
| Tumor PI-9 blocks CTL killing | Hi [CD8] & ICAM-1 expression can restore low-avidity CTL recognition and lysis by stabilizing weak interactions between TCR and MHC + self-peptide |
| T-regulatory cells block CTL | Hi $CD4^{Helper}$ cells overcome $CD4^{Reg}$ cells |

In primary infections, the death rate from DV is very low (1 in 61,000 per Manson's Tropical Diseases). The virus infects but does not kill APC of the monocyte-macrophage and Dendritic Cell lineage. These infected APC then begin a cytokine cascade of the pro-inflammatory (TNF-alpha and IL-1 beta), and $T_H1$ (IL-2, IL-7, IL-12, IL-15, and IL-21) types. These cytokines result in strong activation of both the adaptive (CTL) and innate (NK) immune systems. After a 3-5 day incubation period, the fever rises to 39.5-40.5° C., and remains elevated for 4-5 days. The patient experiences intense headache, joint pain, malaise, and sensitivity to light. A rash covering the chest back and sometimes legs and arms develops by day 3 of fever. Clinically, dengue infections result in lowered platelet counts leading to hemorrhage, which ranges from minor to life-threatening in case of shock syndrome. With proper supportive care based on judicious fluid management, recovery is complete in 99% of cases.

Expression of genes in cells of the subject may be increased by DV infection, including, but not limited to, IL-1 beta, IL-2, IL-7, IL-12, IL-15, IFN-alpha, IFN-gamma, TNF-alpha, TNF-beta, GM-CSF, CD8 antigen, ICOSLG, CCL3, CCL5, TRAIL, IP10, GNLY, GZMA, HLA-DRA, HLA-DP alpha1, HLA-DP beta 1, and ZAP70. Increased levels of proteins corresponding to these genes may be observed in circulating fluids of the subject. Levels may be increased at least 2-fold. Levels may be increased between 2-fold and 1000-fold. Levels may be increased between 2-fold and 100-fold. Levels may be increased between 2-fold and 10-fold. Cell types of a subject administered DV may be increased by DV infection, including, but not limited to, CD8+CD44+62L-cells, CD4+CD44+CD62L$^{lo}$ cells, HLA-DR+CD8+ cells, Tia-1 CD8+ cells, VLA-4 CD8+ cells, ICAM-1 CD8+ cells, and LFA-1 CD8+ cells. In some instances, TNF-α, is released by the immune system during DV infection. TNF-α is an inflammatory cytokine with pleiotropic effects, including direct killing of tumor cells via TRAIL (TNF-Apoptosis-Inducing-Ligand).

In some instances, DV induces high levels of soluble TRAIL (sTRAIL) from a variety of cells including γδCTL, activated M1 macrophages and plasmacytoid DC (pDC). In some instances, DV activates IFNβ, a multifunctional cytokine with a 10-fold higher affinity for the same receptor as IFNα. IFNβ has similar antiviral properties in suppressing transcription of viral RNA, but is much more potent than IFNα in inducing apoptosis in tumor cells. Nitric oxide and IFNβ could act in a synergistic fashion during dengue infection. These molecules may work in tandem to overcome resistance to apoptosis mediated by the high levels of sTRAIL induced by $M_1$ macrophages, pDC, and δγ CTL.

Cancer

Methods described herein provide for treating a subject for cancer. Methods described herein also provide for clearing cancer cells. In some instances, administering DV to the subject induces an immune response. In some instances, the immune response is potent as compared to a common virus, such as a common cold virus. In some instances, the immune response results in tumor regression.

DNA microarray analyses have revealed that hundreds of genetically distinct tumor clones may exist in a single patient with advanced tumor. There is a pattern of negative correlation between $O_2$ supply and genetic mutation rates. The majority of agents such as cytotoxic drugs, antibodies, and small molecules, are nearly always blood-borne, exerting a Darwinian selective pressure to tumor clones that evade therapeutic mechanisms. Clones with the lowest perfusion rates have both low drug exposure and high capacity to evade immune system detection, making them resistant to conventional therapies. Provided herein are methods for cancer cell targeting, comprising inducing fever hyperthermia by administering DV to the subject with cancer, starving low-flow, resistant clones with mutated phenotypes, leaving more genetically stable clones for elimination by activated lymphocytes and other arms of the immune system. In some instances, the methods comprise combining fever with activation of CTL and lymphokine-activated killer cells (LAK) by administering pulsed DCs, lead to higher response rates than with conventional cancer therapies (e.g. antibody drug conjugates, kinase inhibitors, small molecules, etc.) or CTLs alone. The immune suppression seen in patients with advanced cancer is a complex and dynamic process. It involves tolerance to the tumor antigens themselves, which are usually recognized as "self" by CTL. In some instances, methods described herein comprise breaking this tolerance and achieving high levels of $T_H1$ cytokines, which DV infection induces.

Cancers targeted herein may be a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, sarcomas, carcinomas, lymphomas or leukemias. In some instances, the cancer is a solid tumor or a liposarcoma.

In some instances, the cancer is a sarcoma. The sarcomas may be a cancer of the bone, cartilage, fat, muscle, blood vessels, or other connective or supportive tissue. In some instances, sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma). The sarcoma may comprise a Ewing's sarcoma.

In some instances, the cancer is a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instance, the cancer is a neuroendocrine cancer. In some instances, the cancer is a pancreatic cancer, thyroid cancer, or a prostate cancer. In some instances, the cancer is an epithelial cancer, breast cancer, endometrial cancer, ovarian cancer, stromal ovarian cancer, or cervical cancer. In some instances, the cancer is a skin cancer. In some instances, the cancer is a neo-angiogenic skin cancer. In some instances, the cancer is a melanoma. In some instances, the cancer is a kidney cancer, a lung cancer. Exemplary lung cancers include, without limitation, a small cell lung cancer or a non-small cell lung cancer. In some instances, the cancer is a colorectal cancer, e.g., a gastric cancer or a colon cancer. In some instance, the cancer is a brain cancer. In some instances, the cancer is a brain tumor. In some instances, the cancer is a glioblastoma or an astrocytoma.

In some instances, the cancer is a lung cancer. In some instances, the lung cancer is a non-small cell lung carcinoma (NSCLC), small cell lung carcinoma, or mesotheliomia. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). In some instances, the mesothelioma is due to asbestos exposure.

In some instances, the cancer is a central nervous system (CNS) tumor. In some instances, the CNS tumor is classified as a glioma or nonglioma. In some instances, the glioma is malignant glioma, high grade glioma, diffuse intrinsic pontine glioma. Examples of gliomas include astrocytomas, oligodendrogliomas (or mixtures of oligodendroglioma and 13mmune1313oma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

In some instances, the cancer is a blood cancer. In some instances, the cancer is leukemia. In some instances, the cancer is a myeloid leukemia. In some instances, the cancer is a lymphoma. In some instances, the cancer is a non-Hodgkin's lymphoma. In some instances, the cancer is selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, 14mmune14 lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. In some instance, the cancer is a hematological malignancy. In some instance, the hematological malignancy is a B cell malignancy. In some instance, the cancer is a chronic lymphocytic leukemia. In some instance, the cancer is an acute lymphoblastic leukemia. In some instance, the cancer is a CD19-positive Burkitt's lymphoma. In some instance, the leukemia is an acute lymphocytic leukemia, acute myelocytic leukemia, chronic lymphocytic leukemia, or chronic myelocytic leukemia. Additional types of leukemias include, but are not limited to, hairy cell leukemia, chronic myelomonocytic leukemia, and juvenile myelomonocytic leukemia.

In some instance, the lymphoma develops from a B lymphocyte or T lymphocyte. Two major types of lymphoma are Hodgkin's lymphoma, previously known as Hodgkin's disease, and non-Hodgkin's lymphoma. In some instance, the Non-Hodgkin lymphoma is indolent. In some instance, the Non-Hodgkin lymphoma is aggressive. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Methods of Administration

Provided herein are methods comprising administering Dengue virus and dendritic cells to a subject in need thereof. In some instances, the virus is provided in an aqueous form. In some instances, the virus is lyophilized and reconstituted in an aqueous solution (e.g., saline solution). In some instances, the virus is administered by a route selected from subcutaneous injection, intramuscular injection, intradermal injection, percutaneous administration, intravenous ("i.v.") administration, intranasal administration, intralymphatic injection, and oral administration. In some instances, the subject is infused with the virus by an intralymphatic microcatheter.

In some instances, the Dengue virus is initially administered at least 24 hours before administering the dendritic cells. In some instances, the Dengue virus is initially administered between about 12 hours and about 96 hours before administering the dendritic cells. In some instances, the Dengue virus is initially administered between about 24 hours and about 72 hours before administering the primed dendritic cells. In some instances, the Dengue virus is initially administered between 1 day and 4 days before administering the primed dendritic cells. In some instances, the Dengue virus is administered only once. In some instances, the Dengue virus is administered more than once. In some instances, the Dengue virus is administered only before receiving dendritic cells. In some instances, the Dengue virus is administered after receiving the primed dendritic cells. In some instances, the Dengue virus is administered before and after receiving the primed dendritic cells.

In some instances, the methods comprise administering the Dengue virus at a dose of about 0.5 ml of $10^6$ pfu/ml. In some instances, the dose is between about $10^3$ pfu/ml and about $10^8$ pfu/ml. In some instances, the dose is between about $10^3$ pfu/ml and about $10^6$ pfu/ml.

In some instances, successful infection or inoculation of the subject with the Dengue virus is confirmed by the development of hyperthermia or fever. In some instances, successful infection or inoculation of the subject with the Dengue virus is confirmed by the presence or increase of circulating cytokines in the blood/plasma of the subject. Cytokines may include, but are not limited to, interleukin-2 and interferon-gamma.

In some instances, methods described herein comprise administering primed dendritic cells to a subject in need thereof only once. In some instances, the primed dendritic cells are administered more than once. In some instances, the primed dendritic cells are administered a first time and a second time, wherein the first time and the second time are separated by about 1 day, about 2 days, about 3 days, about 4 days, about 5 days, or about 6 days, about 8 days, about 10 days, about 12 days, or about 18 days. In some instances, the first time and the second time are separated by about 1 week, about 2 weeks, about 3 weeks, or about a month. In some instances, the first time and the second time are separated by more than a month. In some instances, the first time and the second time are separated by less than 12 months. In some instances, the first time and the second time are separated by more than 12 months.

In some instances, methods described herein provide for administering primed dendritic cells to a subject when the subject is hyperthermic. In some instances, primed dendritic cells are administered after the subject has spike a fever. In some instances, primed dendritic cells are administered after the subject's temperature has risen to between about 37.5° C. and about 42° C. In some instances, the primed dendritic cells are administered after the subject's temperature has risen to between about 38° C. and about 42° C. In some instances, the primed dendritic cells are administered after the subject's temperature has risen to at least about 38.5° C. In some instances, the primed dendritic cells are administered after the subject's temperature has risen to 38.5° C. In some instances, the subject's temperature is measured by a tympanic or oral method.

EXAMPLES

Example 1. Generation and Pulsing of Dendritic Cells (DC)

A method described by Lutz M., et. Al. (J. Immunol. Methods 223:77-92, 1999), was employed to generate mature DC form mouse bone marrow. Bone marrow suspensions were incubated in petri dishes in medium supplemented with recombinant murine GM-CSF for 10 days. Non-adherent cells were collected, centrifuged and resuspended in medium containing GM-CSF and lipopolysaccharide. Two days later, the DCs were harvested and their viability was determined by trypan-blue exclusion. Purity of the DC was determined by flow cytometry analysis. DCs were pulsed with the synthetic peptides at 10 µg/ml for 18 hours. After 18 hours of incubation, DCs were harvested, washed twice in HBSS, and resuspended in HESS for additional studies (see Example 2 and 3).

Figure 2:
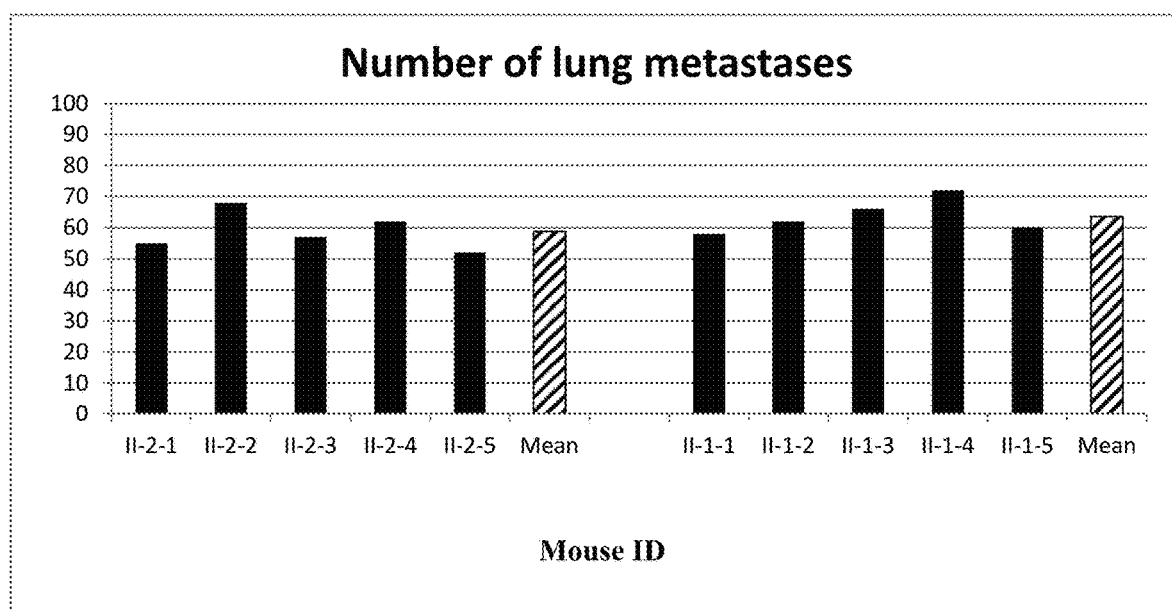
FIG. 2 shows a plot of corresponding to the number of lung metastases from melanoma cells in mice under various treatment conditions. The patterned bars represent the mean number of lung metastases for each condition.

Example 2. Dengue Virus and Dendritic Cells for the Treatment of Melanoma in a First Mouse Model A mouse model assay was performed to observe results from combination targeting of cancer cells using a Dengue virus (DV) strain and tumor antigen primed dendritic cells (DCs). DV C57BL/6 mice were inoculated with 0.05 ml of Dengue virus (DEN-2 strain #1710) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 (rIL-2) and 500 1U (rIFN-gamma) on days 5, 10, 15, and 20 following administration of Dengue virus (DEN-2 strain #1710, CDC database entry number 555, provided by Dr. Duane Gubler). Seven days after the Dengue virus administration, C57BL/6 mice were immunized with mouse DC incubated with the 2 peptides separately and injected intravenously. Peptides were synthesized. The H-2b-restricted peptide from Ovalbumin (OVA-8), SIINFEKL (SEQ ID NO: 7), was used as a control. B16 melanoma-associated H-2b-restricted peptides derived from the antigens gp100/pme117 (EGSRNQDWL (SEQ ID NO: 1)) and from TRP-1/75 (TAYRYHLL (SEQ ID NO: 2)) were used to pulse murine DC (see Example 1 for details). Two additional immunizations with DC were given at 14-day intervals. Three days after the last DC infusion, mice were challenged with $5\times10^4$ viable B16 melanoma cells intravenously in the lateral tail vein and then followed for survival, which was recorded as the percentage of surviving animals over time (in days) after tumor injection. Data was recorded from five or more mice/group (see Table 3 and FIG. 2).

TABLE 3

| Condition | Group | MOUSE ID | NO. OF LUNG METAS-TASES | Mean |
|---|---|---|---|---|
| DV$10^6$ pfu/ml + 2 × $10^6$ DC pulsed with gp100/TRP2 | 2 | II-2-1 | 55 | |
| DV$10^6$ pfu/ml + 2 × $10^6$ DC pulsed with gp100/TRP2 | 2 | II-2-2 | 68 | |
| DV$10^6$ pfu/ml + 2 × $10^6$ DC pulsed with gp100/TRP2 | 2 | II-2-3 | 57 | |
| DV$10^6$ pfu/ml + 2 × $10^6$ DC pulsed with gp100/TRP2 | 2 | II-2-4 | 62 | |
| DV$10^6$ pfu/ml + 2 × $10^6$ DC pulsed with gp100/TRP2 | 2 | II-2-5 | 52 | |
| | | | | 58.8 |
| No DV + 2 × $10^6$ DC pulsed with gp100/TRP2 | 1 | II-1-1 | 58 | |
| No DV + 2 × $10^6$ DC pulsed with gp100/TRP2 | 1 | II-1-2 | 62 | |
| No DV + 2 × $10^6$ DC pulsed with gp100/TRP2 | 1 | II-1-3 | 66 | |
| No DV + 2 × $10^6$ DC pulsed with gp100/TRP2 | 1 | II-1-4 | 72 | |
| No DV + 2 × $10^6$ DC pulsed with gp100/TRP2 | 1 | II-1-5 | 60 | 63.6 |

The number of lung metastases observed in mice administered in Group 2 (Dengue Virus serotype 2 strain #1710 and tumor peptide primed DCs) was 7.5% lower than control mice in Group 1, administered the tumor peptide primed DCs without the Dengue virus.

Example 3. Dengue Virus and Dendritic Cells for the Treatment of Melanoma in a Second Mouse Model A mouse model assay was performed to observe results from combination targeting of cancer cells using a Dengue virus (DV) strain and tumor antigen primed dendritic cells (DCs). Mice were administered cytokines to parallel the response to DV observed in humans.

Tumors were established in mice using the H-$^2$b-restricted B16 murine melanoma cells line (ATCC #CRL-6322). Peptides (B16 melanoma associated H-$^2$b-restricted peptides derived from antigens gp100/pme117 and from TRP-1/gp75) used for pulsing the dendritic cells were synthesized.

Dendritic cells were generated from mouse bone marrow according to the method described in Lutz et al. (J. Immunol. Methods 223:77-92, 1999).

On day 0, mice received $5 \times 10^4$ viable B16 melanoma cells intravenously in the lateral tail vein to establish pulmonary metastases. On day 7, the mice were inoculated with 0.05 ml of Dengue virus (DEN-2 strain #1710, CDC database entry number 555) at $1 \times 10^6$ or $1 \times 10^7$ pfu/ml by injection in the base of tail. Recombinant murine IL-2 (Genzyme) and IFN-gamma (Sigma Pharmaceuticals) were administered by intravenous infusion at 2,000 1U (rIL-2) and 500 1U (rIFN-gamma) at 5-day intervals following administration of Dengue virus (DEN-2 strain #1710). On days 21, 35 and 49, the mouse DC were incubated with the 2 peptides separately and injected intravenously in 2 sequential administrations on the same day to match the route and schedule of administration in patients (see Example 2 for additional details). Control groups of mice received no Dengue virus or dendritic cells pulsed with H-$^2$b-restricted peptide from ovalbumin (OVA-8), SIINFKEL Treatment and control groups are shown in Table 4.

TABLE 4

| Dengue Virus | # of dendritic cells and type of peptide |
|---|---|
| Group A | |
| $10^6$ pfu/ml | $10^6$ DC pulsed with gp100/pme117 (EGSRNQDWL) (SEQ ID NO: 1) |
| | $10^6$ DC pulsed with TRP-1/gp75 (TAYRYHLL) (SEQ ID NO: 2) |
| Total | $2 \times 10^6$ DC pulsed with peptide/mouse |
| Group B | |
| $10^6$ pfu/ml | $10^7$ DC pulsed with gp100/pme117 (EGSRNQDWL) (SEQ ID NO: 1) |
| | $10^7$ DC pulsed with TRP-1/gp75 (TAYRYHLL) (SEQ ID NO: 2) |
| Total | $2 \times 10^7$ DC pulsed with peptide/mouse |
| Group C - Control | |
| None | $10^6$ DC pulsed with gp100/pme117 (EGSRNQDWL) (SEQ ID NO: 1) |
| | $10^6$ DC pulsed with TRP-1/gp75 (TAYRYHLL) (SEQ ID NO: 2) |
| Total | $2 \times 10^6$ DC pulsed with peptide/mouse |
| Group D - Control | |
| $10^6$ pfu/ml | $10^6$ DC pulsed with OVA (SIINFKEL) (SEQ ID NO: 7) |
| | $10^6$ DC pulsed with OVA (SIINFKEL) (SEQ ID NO: 7) |
| Total | $2 \times 10^6$ DC pulsed with peptide/mouse |

Figure 3:
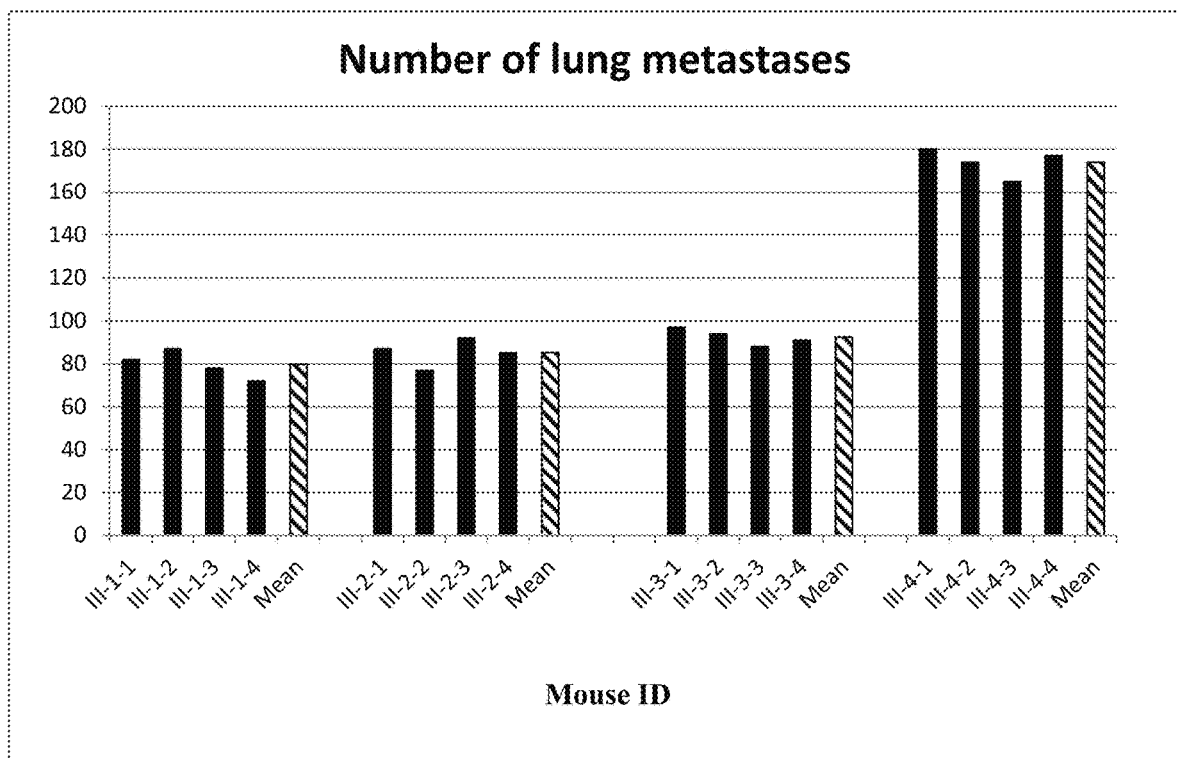
FIG. 3 shows a plot of corresponding to the number of lung metastases from melanoma cells in mice under various treatment conditions. The patterned bars represent the mean number of lung metastases for each condition.

On day 90, animals were sacrificed and lung tumor colonies were counted. Pulmonary metastases were enumerated in a blinded, coded fashion after insufflation and fixation of the lungs with Fekette's solution. Data were reported as the mean number of metastases; four mice/group (see Table 5 and FIG. 3). Histopathology of the following major organ systems were performed: brain, heart, lungs, liver, kidneys, spleen and gonads (data not shown).

TABLE 5

| Condition | Group | MOUSE ID | NO. OF LUNG METAS-TASES | Mean |
|---|---|---|---|---|
| DV$10^6$ pfu/ml + $2 \times 10^6$ DC pulsed with gp100/TRP2 | A | III-1-1 | 82 | |
| DV$10^6$ pfu/ml + $2 \times 10^6$ DC pulsed with gp100/TRP2 | A | III-1-2 | 87 | |
| DV$10^6$ pfu/ml + $2 \times 10^6$ DC pulsed with gp100/TRP2 | A | III-1-3 | 78 | |
| DV$10^6$ pfu/ml + $2 \times 10^6$ DC pulsed with gp100/TRP2 | A | III-1-4 | 72 | |
| | | | | 79.75 |
| DV$10^7$ pfu/ml + $2 \times 10^6$ DC pulsed with gp100/TRP2 | B | III-2-1 | 87 | |
| DV$10^7$ pfu/ml + $2 \times 10^6$ DC pulsed with gp100/TRP2 | B | III-2-2 | 77 | |
| DV$10^7$ pfu/ml + $2 \times 10^6$ DC pulsed with gp100/TRP2 | B | III-2-3 | 92 | |
| DV$10^7$ pfu/ml + $2 \times 10^6$ DC pulsed with gp100/TRP2 | B | III-2-4 | 85 | |
| | | | | 85.25 |
| No dengue virus + $2 \times 10^6$ DC pulsed with gp100/TRP2 | C | III-3-1 | 97 | |
| No dengue virus + $2 \times 10^6$ DC pulsed with gp100/TRP2 | C | III-3-2 | 94 | |
| No dengue virus + $2 \times 10^6$ DC pulsed with gp100/TRP2 | C | III-3-3 | 88 | |
| No dengue virus + $2 \times 10^6$ DC pulsed with gp100/TRP2 | C | III-3-4 | 91 | |
| | | | | 92.5 |
| DV$10^6$ pfu/ml + $2 \times 10^6$ DC pulsed with OV | D | III-4-1 | 180 | |
| DV$10^6$ pfu/ml + $2 \times 10^6$ DC pulsed with OV | D | III-4-2 | 174 | |
| DV$10^6$ pfu/ml + $2 \times 10^6$ DC pulsed with OV | D | III-4-3 | 165 | |
| DV$10^6$ pfu/ml + $2 \times 10^6$ DC pulsed with OV | D | III-4-4 | 177 | |
| | | | | 174 |

The number of lung metastases observed in mice in Group C (administered tumor antigen primed DCs and no virus) was 47% less than control Group D (administered DENV-2 #1710 and DCs exposed to a control peptide). The number of lung metastases observed in mice in Group A (administered DENV-2 #1710 and tumor antigen primed DCs) was 54% less than control Group D (administered DENV-2 #1710 and DCs exposed to a control peptide). The number of lung metastases observed in mice in Group B (administered DENV-2 #1710 and tumor antigen primed DCs) was 51% less than control Group D (administered DENV-2 #1710 and DCs exposed to a control peptide). The average reduction in Group A and B compared to Group D was 52.8%.

Example 4. Manufacture and Use of Dengue Virus

A Master Cell Bank with validated and certified cell lines from Vero (African Green Monkey Kidney Cells) is set up and tested for absence of any contaminants and adventitious organisms. Vero lines are used by the World Health Organizations to produce a variety of viral vaccines. Dengue virus is passaged in a validated Vero Line derived from the Master Cell Bank and established as a Working Cell Bank according to guidelines established by the FDA Center for Biologics (CBER). Dengue Virus Type 1, 2, 3, or 4 from initial seed stock are added to the Vero Cells of the WCB at a MOI of $10^{-5}$.

The first 4-ml overlay medium-containing 1% SeaKem LE agarose (FMC BioProducts, Rockland, Me.) in nutrient medium (0.165% lactalbumin hydrolysate [Difco Laboratories, Detroit, Mich.]), 0.033% yeast extract [Difco], Earle's balanced salt solution, 25 mg of gentamicin sulfate [Bio-Whittaker, Walkersville, Md.] and 1.0 mg of amphotericin B [Fungizone; E. R. Squibb & Sons, Princeton, N.J.], per liter and 2% FBS)—is added after adsorption of the 200-ml virus inoculum for 1.5 h at 37° C. Following incubation at 37° C. for 7 days, a second 2-ml overlay containing additional 80 mg of neutral red vital stain (GIBCO-BRL, Gaithersburg, Md.) per ml is added. Plaques are counted 8 to 11 days after infection.

A plaque assay on final virus cultures is performed, with a target of $10^6$ pfu/ml as a standard dose. Ultracentrifugation is used to concentrate virus if this target is not reached. Following confirmation of virus titer, final product is filtered to remove any cellular debris, tested for absence of any adventitious organisms, and upon final lot released, bottled in 5 ml bottles with a label as a BSL-2 level pathogen, and stored at 4° C. until ready for shipment and administration.

Example 5. Manufacture and Use of Dendritic Cells Pulsed with Tumor Antigens

Monocytes are separated from other white blood cells (e.g. T cells. B cells, NK cells, eosinophils and basophils). This is accomplished with immune-magnetic selection or, alternatively, by adherence properties. Immuno-magnetic selection involves pouring the white blood cells into a sterile plastic column with plastic beads coated with antibodies for immune cell CD surface proteins: (CD4/CD8/CD56, etc.). The unwanted cells adhere to the beads leaving the monocytes to pass through and be collected. In positive selection, magnetic beads coated with CD1+/CD14+ capture the monocytes, a magnet is placed against the column, and unwanted cells are flushed out of the column with PBS solution. The monocytes are then washed off the beads for the next step. In adherence selection, the properties of monocytes to stick to certain surfaces are used to separate them by running the apheresis product down a slanted column.

Alternatively, bone marrow cells are depleted for lymphocytes and MHC Class positive cells by Fluorescent Activated Cell Sorting (FACS) with monoclonal antibodies for CD3, CD4, and CD8. Remaining cells are cultured overnight in Iscove's modified Dulbecco's medium (IMDM) supplemented with 10% Fetal Calf Serum (FCS), 2-ME, and 100 IU/ml penicillin, 1 mM sodium pyruvate, and 10 uM nonessential amino acids at 37° C. in a 5% $CO_2$ atmosphere in 24-well plates with approximately 1 million cells in 1 ml culture medium/well. After 24 hours, the cells are replated and cultured in the presence of Granulocyte-Macrophage Colony Stimulation Factor (GM-CSF), and recombinant IL-4 at 900 U/ml. After 3 to 4 days, media to be exchanged for fresh cytokine media.

Alternatively, dermal dendritic cells (DDC) are prepared using the following methods: Keratomes from healthy human volunteers are incubated in a solution of the bacterial proteases Dispase type 2 at a final concentration of 1.2 U/ml in RPMI 1640 for 1 hour at 37° C. After the incubation period, epidermis and dermis are easily separated. Epidermal and dermal sheets are then cut into small (1-10 mm) pieces after several washing with PBS, and placed in RPMI 1640 supplemented with 10% Fetal Bovine Serum (FBS), and placed in 10-cm tissue culture plates. After 2-3 days, pieces of tissue are removed, and the medium collected. Cells migrating out of the tissue sections into the medium are spun down, resuspended in 1-2 ml fresh medium and stained with trypan blue. Further enrichment is achieved by separation on a metrizamide gradient. Cells are layered onto 3-ml columns of hypertonic 14.5% metrizamide and sedimented at 650 g for 10 minutes at room temperature. Low density interphase cells are collected and washed in two successively less hypertonic washes (RPMI 1640 with 10% FBS and 40 mM NaCl) to return cells to isotonicity.

When the monocytes are collected, they may number only a few thousand. The recombinant human growth factors rhuInterleukin-4 (IL-4), and rhuGranulocyte-Macrophage-Colony-Stimulation Factor (GM-CSF), are used in a multi-step protocol to accomplish the expansion of DC numbers to the range of 50 million. The addition of IL-4 and GM-CSF expands the numbers and the development of mature-DC markers: ($CD11^+$, $CD80^+$, $CD83^+$), as well as increased expression of both Class I (for presentation of short peptides to $CD8^+$, and Class II MEW complexes (for presentation of longer peptides to $CD4^+$ Helper-Inducer T lymphocytes). After approximately 4 days, the number of mature DCs will be measured.

Pulsing the Dendritic Cells

Whole autologous tumor cell lysate is prepared by several methods. The development of automated cell processors like the Miltenyi GentleMACS system allows the sample to be manually minced, suspended in PBS solution, then a pre-selected tissue-specific software-controlled rotor system separates the tumor cells. The single-cell suspension can be membrane-lysed with minimal damage to tumor peptides. Alternatively, the sample does not separate the tumor cells. Instead the sample is left to contain tumor cells and supporting cells (e.g. cells from the tumor microenvironment). Cells are lysed with $NH_4Cl$ to eliminate red blood cells and produce apoptotic and necrotic bodies without destroying peptides needed for CTL induction.

After addition of the lysate, the DCs engulf and process the peptides for presentation to CTL. The final step is the maturation with an inflammatory signal. A preferred agent is Lipopolysaccharide (LPS) from bacterial cell walls. After exposure to LPS, the DC up-regulate their $CD80/CD83^+$ activation markers, increase production of IL-12p70 to induce a Type 1 CTL response, and become resistant to further antigen uptake and processing.

After final sterility, specificity, and viability testing, the DC are transferred to polymer bags suitable for freezing at −70° C. in liquid $N_2$, storage up to 1 year, and shipping to the clinic for use. The bags are shipped cool overnight, then re-warmed to 37° C. in a warm-water bath before intravenous administration with a 0.9% NaCL solution concurrent. The i.v. DCs traffic to the lungs, where some will be trapped, but the majority will pass to secondary lymphatic organs such as liver and spleen white pulp T-cell zones to prime the CTL.

Example 6. Combination Delivery for Treatment of Cancer

Administration of the Dengue Virus is similar to that of other viral vaccine injections. A subject has an area of skin in the shoulder (deltoid) region cleaned with alcohol, then 0.5 ml of the virus is injected under the skin to mimic a mosquito bite. Once the subject has a fever the reaches 38.5° C., after 2-3 days from DV injection, the patient is infused by intralymphatic microcatheter with pulsed (primed) dendritics. Injections are repeated until the patient is negative for disease. DC fusions will use cells manufactured in Example 5.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for reducing or treating cancer, comprising:

(a) subcutaneously administering to a subject an effective amount of Dengue Virus as an adjuvant to an immunotherapy for treatment of cancer, wherein the Dengue Virus is present in a concentration of from $10^3$ pfu/ml to $10^8$ pfu/ml, and wherein the subject has a cancer; and (b) administering autologous dendritic cells to the subject.

2. The method of claim 1, wherein the Dengue Virus is a DENV-1, 2, 3 or 4 serotype.

3. The method of claim 1, wherein the Dengue Virus is not attenuated.

4. The method of claim 1, wherein the cancer is a solid cancer or a blood cancer.

5. The method of claim 1, wherein the autologous dendritic cells are bone-marrow-derived cells.

6. The method of claim 1, wherein the autologous dendritic cells are peripheral-blood-derived cells.

7. The method of claim 1, further comprising obtaining precursors to dendritic cells from the subject, wherein the precursors to dendritic cells comprise CD34+ progenitor cells or CD1+CD14+ immature monocytes.

8. The method of claim 7, further comprising culturing the precursors in the presence of GM-CSF to obtain dendritic cells.

9. The method of claim 1, wherein the autologous dendritic cells are primed against at least one peptide tumor cell antigen.

10. A method for reducing or treating cancer, comprising:

(a) subcutaneously administering to a subject an effective amount of Dengue Virus as an adjuvant to an immunotherapy for treatment of cancer, wherein the Dengue Virus is present in a concentration of from $10^3$ pfu/ml to $10^8$ pfu/ml, and wherein the subject has a cancer; and (b) administering allogeneic dendritic cells to the subject.

11. The method of claim 10, wherein the Dengue Virus is a DENV-1, 2, 3 or 4 serotype.

12. The method of claim 10, further comprising obtaining precursors to dendritic cells from the subject, wherein the precursors to dendritic cells comprise CD34+ progenitor cells or CD1+CD14+ immature monocytes.

13. The method of claim 10, wherein the cancer is a solid cancer or a blood cancer.

14. The method of claim 10, wherein the Dengue Virus is not attenuated.

15. The method of claim 1, wherein the Dengue Virus is isolated from a Vero cell line.

16. The method of claim 10, wherein the Dengue Virus is isolated from a Vero cell line.

17. The method of claim 10, wherein the allogeneic dendritic cells are bone-marrow-derived cells.

18. The method of claim 10, wherein the allogeneic dendritic cells are peripheral-blood-derived cells.

19. The method of claim 10, wherein the allogeneic dendritic cells are primed against at least one peptide tumor cell antigen.

20. The method of claim 12, further comprising culturing the precursors in the presence of GM-C SF to obtain dendritic cells.

* * * * *